US005632765A

United States Patent [19]

Holder

[11] Patent Number: 5,632,765

[45] Date of Patent: May 27, 1997

[54] CHIROPRACTIC DEVICE FOR REMOVING A VERTEBRAL SUBLUXATION

[76] Inventor: Jack M. Holder, 5990 Bird Rd., Miami, Fla. 33155

[21] Appl. No.: 384,542

[22] Filed: Feb. 7, 1995

[51] Int. Cl.$^6$ .......... A61F 5/00

[52] U.S. Cl. .......... 606/238; 601/108

[58] Field of Search .......... 606/238, 7, 237; 601/97, 101, 105, 108, 110

[56] References Cited

U.S. PATENT DOCUMENTS

| | | | |
|---|---|---|---|
| 2,048,220 | 7/1936 | Redding | 606/238 |
| 2,078,159 | 4/1937 | Redding | 606/238 |

*Primary Examiner*—Michael Powell Buiz
*Assistant Examiner*—Patrick W. Rasche
*Attorney, Agent, or Firm*—Robert M. Downey

[57] ABSTRACT

A chiropractic mallet instrument for delivering a selected impact to the spinal vertebrae and or other bones of a patient in order to remove a vertebral subluxation and or other subluxations includes a tubular housing with a central handle movably supported thereon, a compression spring engaging a latch assembly and an elongate anvil member coaxially and movably fitted within an interior of the housing and extending from one end thereof, the anvil member including a distal end zone with a distal tip structured for removable attachment of various impact heads of different sizes, shapes and densities, the anvil member being axially movable relative to a longitudinal axis of the housing between a retracted, cocked position and an extended, released position. The latch assembly is operably interconnected to the central handle and carries and holds the anvil member in the retracted, cocked position upon movement of the central handle towards a palm handle on an opposite end of the housing. Application of pressure to the distal tip actuates a trigger mechanism, releasing the latch assembly and anvil member, causing the compression spring to urge the anvil member rapidly to the extended, released position. A guide element is selectively positionable within one of three directional grooves in the distal end zone to control rotation of the anvil member when moving to the extended, released position, so that the impact head delivers either a straight axial force or a clockwise or counter clockwise torsional force on impact.

3 Claims, 1 Drawing Sheet

CHIROPRACTIC DEVICE FOR REMOVING A VERTEBRAL SUBLUXATION

FIELD OF THE INVENTION

This invention relates to a chiropractic mallet device, and, more particularly, to an improved chiropractic mallet device having a trigger mechanism to release an anvil member so that a distal end zone of the anvil member having an impact tip attached thereto delivers an impact of a selected force, in a selected rotational direction, wherein a selected torsional or straight axial force may be applied upon impact to a patient's spinal column to reduce or remove a vertebral subluxation and other subluxations.

BACKGROUND OF THE INVENTION

In the field of medicine, there is a growing recognition that it is important that the joint of a person especially those of the spine, be in proper position for better mental and physical health. Indeed, the recognized and growing medical field of chiropractic involves methods for treating various ailments by adjustments of the joints, especially the spinal vertebrae, (subluxations).

It will be appreciated that, because there are many practitioners in the field of chiropractic, there are also many different variations in the actual performance of any given common recognized chiropractic technique. For example, the degree of force and direction of force applied to a patient in performing a recognized adjustment technique often varies from one practitioner to another practitioner due to human error, variances in size and strength and other variables which, inevitably yields in variable results. Accordingly, there has long been an appreciation of the fact that it would be generally beneficial to practitioners and patients alike if a successful adjustment technique could be reproduced by a broad spectrum of practitioners in a more uniform and consistent manner to provide more predictable and reproducible results.

It has been discovered that an instrument designed to deliver an impact to the spinal vertebrae is useful in attempting to achieve more consistent results of spinal adjustments. Thus, impact or mallet type instruments have been used in the chiropractic field. Specifically, there have been impact or mallet type instruments in the past which include a housing, a piston with an exposed impact head and an opposite end captivated in the housing, spring means in the housing engaging the piston and normally urging it to an extended normal position so that the piston can be forced axially to a retracted position, compressing the spring to a predetermined position and thereafter releasing the piston to the extended position. A representative mallet instrument of this type is disclosed in U.S. Pat. No. 2,421,354 to Reiter, directed to a surgical mallet instrument. Instruments of the same mechanical structure as the Reiter instrument, as well as modified instruments, have been used in the chiropractic field to perform adjustments of the spinal vertebrae. The piston and impact heads of these instruments releases automatically when the piston is pulled back against the spring to a predetermined position, at which point the piston and impact head are released outwardly to deliver a straight axial impact force. Thus, these instruments do not provide any means for "cocking" the piston or a trigger mechanism activated by external pressure to the distal tip of the piston for releasing the cocked piston. The amount of force delivered by the impact head cannot be adjusted, as the spring is compressed to the same level each time the piston reaches the predetermined release position. Further, the distal tip of the piston of these instruments is not structured for removable attachment of various impact heads of different sizes, shapes and densities, nor are they structured for selective clockwise or counterclockwise rotation of the distal tip to provide a torsional impact force.

SUMMARY OF THE INVENTION

The present invention is directed to an improved chiropractic mallet instrument for delivering an impact of selected force to the spinal vertebrae and other bones of a patient in order to remove a vertebral subluxation and other subluxations.

The instrument includes tubular housing with a central handle movably supported thereon, a compression spring engaging a latch assembly, and an elongate anvil member coaxially and movably fitted within an interior of the housing and extending from one end thereof. The anvil member includes a distal end zone with a distal tip structured for removable attachment of various impact heads of different sizes, shapes and densities. The anvil member is axially movable relative to a longitudinal axis of the housing between a retracted, cocked position against a force of the compression spring, and an extended, released position. The latch assembly is operably connected to the central handle and carries and holds the anvil member in the retracted, cocked position upon movement of the central handle towards a palm handle on an opposite end of the housing. Application of pressure to the distal tip activates a trigger mechanism which releases the anvil member, resulting in the compression spring forcing the anvil member rapidly outward, relative to the end of the housing to the extended position. Torque control means include a guide element at the end of the housing which is selectively positionable within one of three directional grooves formed in the distal end zone of the anvil member. Depending upon which groove the guide element is positioned in, the distal end zone of the anvil member will be caused to twist in either a clockwise or counter clockwise direction, or in a straight axial direction upon release from the cocked position to the extended position. In this manner, a clockwise torsional force, counter clockwise torsional force or straight axial force can be selectively delivered by the impact head to the adjustment site. In order to control the amount of force delivered by the impact head, the housing is provided with a screw cap on the opposite end to vary the amount of compression of the compression spring.

There are features of the present invention, in its several embodiments, which improve upon mallet or impact delivering instruments in the related art. Generally, the improving features of the present invention include singularly or in combination;

a) torque means to selectively cause either a clockwise twist, a counter clockwise twist or straight, non-twisting axial movement of the piston head;

b) latch means to hold the anvil member in a cocked position so that energy stored in the compression spring is not automatically released at completion of retraction of the anvil, thereby holding the anvil member in a "cocked" position to be released upon activation of the trigger means;

c) a pressure sensitive trigger means to "fire" the anvil member once located and orientated at the desired position on the patient;

d) means for selectively adjusting compression of the compression spring, thereby enabling selective adjustment of the amount of energy stored in the spring when the instrument is "cocked" and, accordingly the amount of force delivered on impact after release of the anvil member; and/or e) a plurality of impact heads each having means for removable attachment to the distal tip of the anvil member and being of different sizes, shapes and densities as may be desired for use in order to achieve a particular result.

BRIEF DESCRIPTION OF THE DRAWINGS

For a fuller understanding of the nature of the present invention, reference should be had to the following detailed description taken in connection with the accompanying drawings in which.

DETAILED DESCRIPTION OF THE PREFERRED EMBODIMENT

Figure 1:
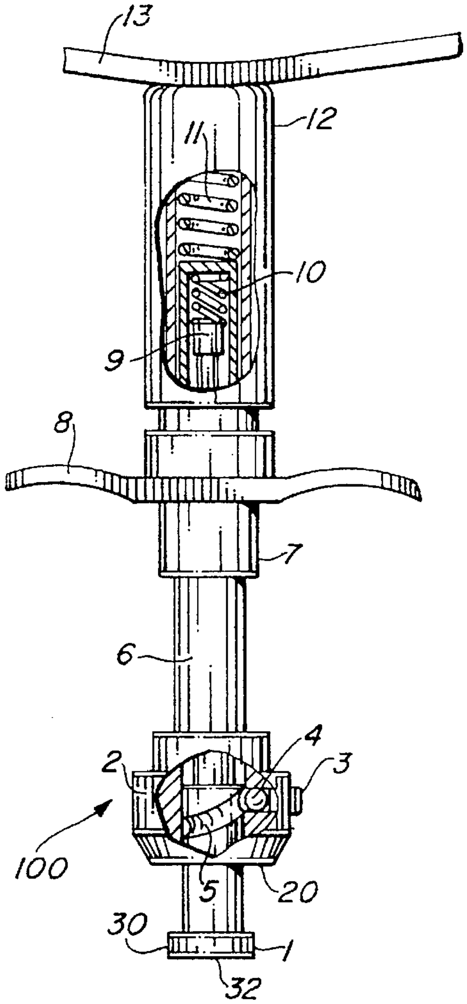
FIG. 1 is a top plan view in partial cutaway, illustrating the mallet instrument of the present invention.

Referring to the several views of the drawings, there is illustrated the chiropractic instrument 100 of the present invention which includes a tubular housing 6 having a central handle 8 movably supported thereon, an end cap 12 threadably fitted to the housing 6 and a compression spring 11 engaging a latch housing 17 and the end cap 12. An elongate anvil member 1 is coaxially and movably fitted within an interior of the housing 6, and extends from a lower end 20 thereof. The anvil member 1 includes a distal end zone 30 with a distal tip 32. The distal tip 32 includes a cavity 34 specifically structured to receive a congruently configured attaching element 36 on various impact heads 40, each being of different size, shape and formed of resilient materials of different densities.

In use, the instrument is held in the user's predominant hand so that the palm handle 13 seats against the palm of the hand. The user's fingers are then wrapped around the center handle 8. Operation begins with the user drawing back the center handle 8 towards the palm of the hand in a cocking motion. This cocking motion of the center handle 8 causes a latch slide 7, movably supported on the handle 8, to move towards the palm handle 13. The latch slide includes a pin 24 which catches a latch housing 17 and moves the latch housing axially with the latch slide upon movement towards the palm handle 13. The latch housing 17 is releasably secured to a latch trigger pin 9 by two latch ball bearings 14. The ball bearings 14 travel axially inside the cavities 28 formed in the latch housing 17. Thus, movement of the latch housing 17 towards the cocked position results in the ball bearing 14 carrying the latch trigger pin 9 axially therewith. As the latch trigger pin 9 travels to the cocked position, it compresses a latch spring 10. Likewise, as the latch housing 17 travels to the cocked position, it compresses a main compression spring 11. The main compression spring 11 stores a force needed to move the anvil member 1 from the cocked position to an extended, relaxed position. The degree of compression, and thus the amount of the stored force, in compression spring 11 can be varied by adjusting the end cap 12 on the housing 6. By rotating the end cap 12, to threadably advance or retreat on the housing, the compression of spring 11 is selectively varied. A lower end of the latch housing 17 includes an inwardly directed flange 50 which grabs an enlarged head 16 on a proximal end of the anvil member 1, causing the anvil member 1 to be carried axially with the latch housing 17 as the latch housing 17 and trigger pin 9 are pulled to the cocked position. Upon movement to the cocked position, the latch ball bearings 14 are moved outwardly from an undercut section 54 of the trigger pin 9, as the latch spring 10 begins to hold the trigger pin 9 from further axial movement with the latch slide 17 and ball bearings 14 continuing to move to the cocked position. As the ball bearings 14 are caused to move along the trigger pin 9, they are urged outwardly into holes 56 in a latch slide 18. The latch sleeve 7 and accordingly, the anvil member 1, are in the cocked position when the latch ball bearings 14 line up within the holes 56 in the latch sleeve 18 which is fixed to the interior of the tubular housing 6. At this point, the latch ball bearings 14 have been moved into position within the cavities 28 and holes 56, and hold the latch housing 17 in the cocked position. The latch housing 17 remains in the cocked position due to the latch bearings 14 being each partially within one of the respective cavities 28 and one of the respective holes 56 of the latch sleeve, and being locked in position by the increased diameter portion of the trigger pin 9 which prevents inward movement and release of the ball bearings 14 from within the holes 56. The latch housing 17 and anvil member 1 remain in the cocked position until pressure is applied to the distal tip or impact head on the distal end zone of the anvil member. Upon applying an axial force to the distal tip, the anvil member 1 forces the trigger pin 9 against the latch spring 10 and the trigger pin 9 is moved axially until the undercut section 54 moves into alignment with the holes 56, at which point the latch ball bearings 14 move inwardly and are released from within the holes 56, resulting in the compression spring 11 thrusting the latch housing 17 outwardly. The trigger pin 9, being now latched to the latch housing 17 by the ball bearings 14 within the undercut section 54, is also thrust forward, thereby striking the anvil member 1 and causing it to be thrust outwardly from the housing 6 to the released, extended position. At the extended position, the flange 50 on the lower end of the latch housing engages a coupling ring 15, fixed to the inner wall of the housing 6, which limits outward axial movement of the latch housing 17 and anvil member 1.

Figure 2:
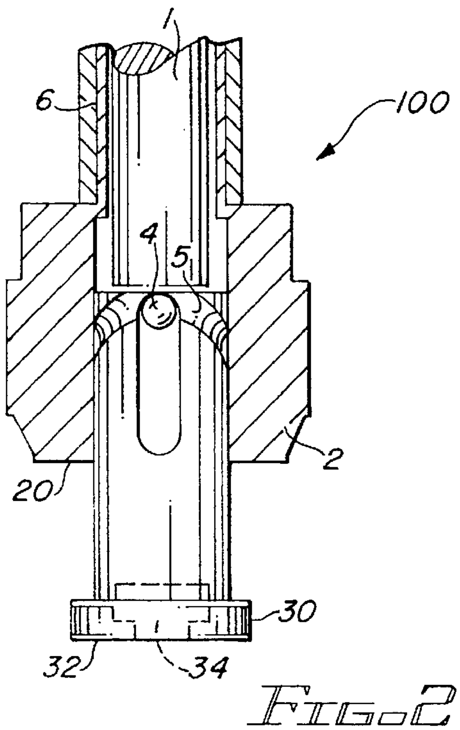
FIG. 2 is an isolated view, in partial section, of a distal end zone of an anvil member shown in relation to a lower end of a housing of the instrument.
Figure 3:
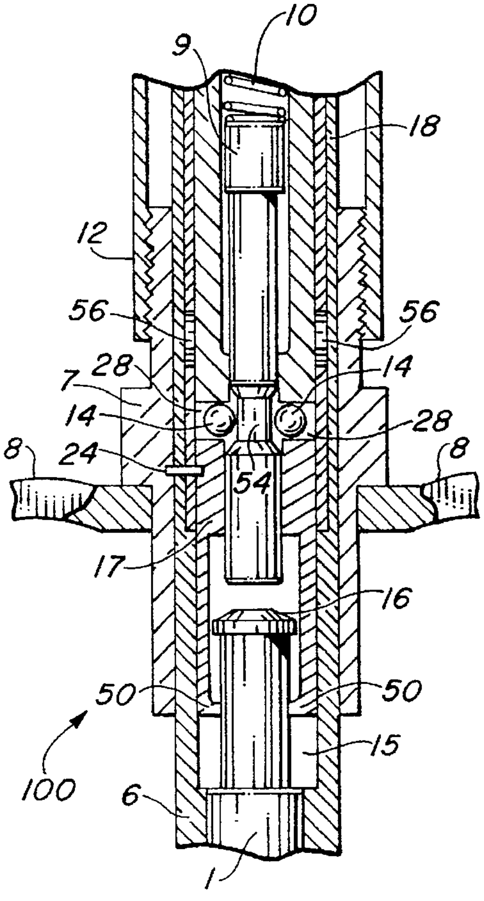
FIG. 3 is an isolated view, shown in cross section, illustrating a latch assembly and trigger assembly of the instrument.
Figure 4:
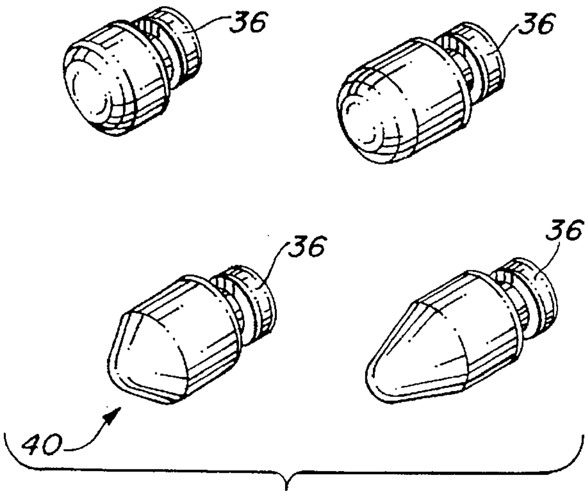
FIG. 4 is a top perspective view of various impact heads for removable attachment on the distal tip of the anvil member.

Prior to release from the cocked position, the user selects the direction of a torsional or non-torsional force to be delivered by the impact head by turning the distal end zone of the anvil member 1 so that a ball bearing 4 is positioned into one of three directional slots 5. The center slot will cause movement of the anvil member 1 in a straight, axial direction. Positioning of the ball bearing 4 in the left slot will result in a twisting movement of the anvil member 1 in the counter clockwise direction (referring to FIG. 2). Positioning of the ball bearing 4 in the right slot (FIG. 2) will result in twisting movement of the anvil member in the clockwise direction to deliver a clockwise torsional force by the impact head. The directional ball bearing 4 is held in position by a retaining screw 3 which is fitted to a bearing retaining sleeve 2 on the end of the housing 6. Accordingly, the twisting or non-twisting motion of the anvil member 1 as it is thrust forward to the extended, released position is controlled by the interaction of the directional ball bearing 4 rolling within one of the three preselected directional slots 5 formed in the distal end zone of the anvil member 1.

What is claimed is:

1. An improved chiropractic device comprising:

a tubular housing including a first end and an opposite second end, a central zone, and a longitudinal axis extending through an interior of said housing between said ends, central handle means movably supported on said housing and exteriorly accessible thereon, an elongate anvil member coaxially and movably fitted within said interior of said housing and extending outwardly from said first end, and being axially movable relative to said longitudinal axis through a predetermined range, between a retracted, cocked position and an extended, released position, said anvil member including a proximal end zone within said housing interior and a distal end zone including a distal end disposed exteriorly of said housing interior, latch means operably interconnected to said central handle means for carrying said anvil member to and holding said anvil member in said retracted, cocked position upon moving said central handle means towards said second end of said housing, release means for operatively disengaging said latch means to cause release of said anvil member from said retracted, cocked position upon application of a predetermined external inwardly directed axial force to said distal end of said anvil member to cause inward axial movement of said anvil member through a predetermined fixed range of movement relative to said housing, biasing means for exerting an axial force on said latch means and said anvil member to cause rapid movement of said anvil member axially outward from said retracted, cocked position to said extended, released position, upon disengaging said latch means by said release means, anvil rotation control means for selectively controlling direction of rotation of said distal end zone of said anvil member about said longitudinal axis when moving towards said extended, released position, said anvil rotation control means including a plurality of directional grooves formed on said anvil member and a guide element structured for selective, operable receipt within a selected one of said plurality of directional grooves, said anvil rotation control means being operable to select one of a plurality of directions of rotation of said distal end zone by turning said distal end zone of said anvil member to move said guide element into a selected one of said plurality of directional grooves, means for selectively varying the axial force exerted on said anvil member by said biasing means, and including a rotating cap threadably attached on said second end of said housing, structured to apply a gradual, progressive compression force or decompression force on said biasing means upon threaded advance or threaded retreat, respectively, on said second end of said housing, a plurality of impact heads each including an attaching element formed thereon for removably attaching selected ones of said plurality of impact heads to said distal end of said anvil member, and said distal end of said anvil member including a cavity formed therein being sized and configured for congruent, releasable attached receipt of said attaching element of a selected one of said plurality of impact heads.

2. The chiropractic device as recited in claim 1 wherein said impact heads are each of a different size, shape and configuration.

3. The chiropractic device as recited in claim 2 wherein said impact heads are each formed of a resilient material of a select one of different densities.

* * * * *